(12) United States Patent
Bychkov et al.

(10) Patent No.: US 11,962,707 B2
(45) Date of Patent: Apr. 16, 2024

(54) AUTHENTICATION OF A VENTILATOR

(71) Applicant: Loewenstein Medical Technology S.A., Luxembourg (LU)

(72) Inventors: Igor Bychkov, Ettlingen (DE); Matthias Schwaibold, Karlsruhe (DE)

(73) Assignee: LOEWENSTEIN MEDICAL TECHNOLOGY S.A., Luxembourg (LU)

(*) Notice: Subject to any disclaimer, the term of this patent is extended or adjusted under 35 U.S.C. 154(b) by 299 days.

(21) Appl. No.: 17/454,654

(22) Filed: Jan. 5, 2022

(65) Prior Publication Data
US 2022/0224544 A1 Jul. 14, 2022

(30) Foreign Application Priority Data
Nov. 19, 2020 (DE) .......................... 102020007090.6

(51) Int. Cl.
*G06F 7/04* (2006.01)
*H04L 9/32* (2006.01)
*H04L 9/40* (2022.01)

(52) U.S. Cl.
CPC ........ *H04L 9/3247* (2013.01); *H04L 63/0428* (2013.01)

(58) Field of Classification Search
CPC . H04L 9/3247; H04L 63/0428; H04L 9/0643; H04L 9/08; H04L 9/0816;
(Continued)

(56) References Cited

U.S. PATENT DOCUMENTS 8,555,070 B2 * 10/2013 Claus ..................... G16H 40/63
713/161
11,596,754 B2 * 3/2023 Hickey ............. A61M 16/0066
(Continued)

FOREIGN PATENT DOCUMENTS

DE 102017002775 A1 9/2018
EP 3340095 A1 6/2018

OTHER PUBLICATIONS

Yaqoob et al., Security Vulnerabilities, Attacks, Countermeasures, and Regulations of Networked Medical Devices—A Review, IEEE, Apr. 30, 2019, pp. 3723-3768. (Year: 2019).*
(Continued)

*Primary Examiner* — Philip J Chea
*Assistant Examiner* — Jenise E Jackson
(74) *Attorney, Agent, or Firm* — Abel Schillinger, LLP

(57) ABSTRACT

Method for authenticating at least one ventilator with at least one remote station, wherein the ventilator can connect itself via at least one interface to the remote station, at least one authentication file is stored on the ventilator, the authentication file contains at least one signature code of a signing authority, and a public keycode of the signing authority is known to the remote station, the ventilator sends the authentication file to the remote station when establishing the connection to the remote station, the remote station checks the signature code of the authentication file using the public keycode as to whether the signature code originates from the signing point and the ventilator is authenticated when the remote station recognizes the signature code as originating from the signing authority.

4 Claims, 7 Drawing Sheets

(58) Field of Classification Search
CPC ... H04L 9/0819; H04L 9/0825; H04L 9/3263; G06F 21/335; G06F 21/35; G06F 21/44; G06F 21/565; G06F 21/6245; G06F 21/64

See application file for complete search history.

(56) References Cited

U.S. PATENT DOCUMENTS

| | | | |
|---|---|---|---|
| 11,672,934 B2* | 6/2023 | Shankaranarayana | A61M 16/0063 128/204.21 |
| 2007/0074027 A1* | 3/2007 | Tung | H04L 9/3247 713/176 |
| 2018/0182473 A1 | 6/2018 | Schwaibold | |
| 2018/0272087 A1* | 9/2018 | Von Blumenthal | A61M 16/104 |
| 2020/0261673 A1* | 8/2020 | Hickey | G16H 20/40 |

OTHER PUBLICATIONS

Hatcliff et al., Rationale and Architecture Principles for Medical Application Platforms, IEEE, Apr. 19, 2012, pp. 1-12. (Year: 2012).*

* cited by examiner

AUTHENTICATION OF A VENTILATOR

CROSS-REFERENCE TO RELATED APPLICATIONS

The present application claims priority under 35 U.S.C. § 119 of German Patent Application No. 10 2020 007 090.6, filed Nov. 19, 2020, the entire disclosure of which is expressly incorporated by reference herein.

BACKGROUND OF THE INVENTION

1. Field of the Invention

The invention relates to a method for authenticating a ventilator with respect to remote stations.

2. Discussion of Background Information

In the case of data transfer between ventilator and servers, as in the case of remote monitoring or telemedicine, highly sensitive data are sometimes transferred, which can include, among other things, data on the health status and the treatment of a patient. It is essentially important here that the ventilators are also assigned a corresponding user upon the data transfer. Several identification methods are known for this purpose from the prior art, which do permit identification of the ventilator, but a secure check of the authenticity of the identity is not provided here, so that other data sources can also impersonate the ventilator and thus, for example, transfer false data.

If one of the hardware components, in particular special components, which are specially configured, is defective, this can result in further problems with respect to the identification, in particular since identification features are also lost due to the defective hardware component.

In view of the foregoing, it would be advantageous to have available a method which enables the secure transfer of data of a ventilator.

SUMMARY OF THE INVENTION

The present invention provides a method for authenticating at least one ventilator with at least one remote station, wherein the ventilator can connect itself via at least one interface to the remote station, wherein at least one authentication file is stored on the ventilator, wherein the authentication file contains at least one signature code of a signing authority and a public keycode of the signing authority is known to the remote station, wherein the ventilator sends the authentication file to the remote station when establishing a connection to the remote station, wherein the remote station checks the signature code of the authentication file using the public keycode as to whether the signature code originates from the signing point, and wherein the ventilator is authenticated when the remote station recognizes the signature code as originating from the signing authority.

In some embodiments of the method, therapeutic data are transferred from the ventilator to the remote station after and/or during the establishment of the connection, wherein the therapeutic data are only processed by the remote station when the ventilator is authenticated. Therapeutic data can thus already be transferred in parallel with the authentication file. However, these data are only processed when the authentication of the ventilator has been carried out.

In some embodiments of the method, the connection from the ventilator to the remote station is only established and/or accepted and/or maintained if the remote station recognizes the signature code as originating from the signing authority and the ventilator is authenticated.

In some embodiments of the method, therapeutic data transferred from the ventilator to the remote station are discarded by the remote station if the remote station does not recognize the signature code as originating from the signing authority.

In some embodiments of the method, the signing authority creates the authentication file and adds the signature code to the authentication file using a private key of the signing authority.

In some embodiments of the method, in addition to the signature code, the authentication file contains at least one identification number of the ventilator, wherein the remote station recognizes the ventilator on the basis of the identification number and assigns it to a user.

In some embodiments of the method, the ventilator generates a request file to request the creation of an authentication file by the signing authority, wherein the request file contains at least the identification number of the ventilator.

In some embodiments of the method, in addition to the request file, the ventilator creates an information file, which contains at least the identification number of the ventilator and at least one identification number of at least one hardware component of the ventilator, wherein the request file and the information file are transferred to a checking unit, the combination of the identification numbers contained in the information file is checked for validity and if the combination of the identification numbers is valid, the checking unit passes on the request file to the signing authority and the signing authority generates the authentication file using the request file.

In some embodiments of the method, the transferred combination of the identification numbers is entered in a database if a combination having an identification number of a hardware component is not yet entered with the identification number of the ventilator. If a combination of the identification number of the ventilator with the identification number of a hardware component is entered, which does not correspond to the transferred combination of the identification numbers, the transferred combination is assessed as nonvalid and the request file is not passed on to the signing authority.

In some embodiments of the method, upon replacement of the hardware component, a new request file is created by the ventilator using at least one identification number of the new hardware component and the identification number of the ventilator.

In some embodiments of the method, the new combination of identification number of the new hardware component and identification number of the ventilator is checked for validity, wherein in the event of a valid new combination of the identification numbers, the request file is transferred to the signing authority, wherein the signing authority creates a new authentication file and adds a signature code to the new authentication file using the private keycode and the new authentication file is then transferred to the ventilator.

In some embodiments of the method, the new combination of ventilator and new hardware component or the identification numbers thereof is checked directly in the signing authority.

In some embodiments of the method, the old combination of the identification numbers of the ventilator and the old hardware component is marked as invalid after replacement of the old hardware component with the new hardware component.

In some embodiments of the method, combinations of ventilators and hardware components marked as invalid are made available to the remote station.

In some embodiments of the method, from time to time the remote station retrieves combinations which are made available and marked as invalid, wherein the remote station does not accept a connection to a ventilator which wishes to authenticate itself using an authentication file which was created using an invalid combination, so that no connection is established between the ventilator and the remote station.

In some embodiments of the method, from time to time the remote station retrieves combinations which are made available and marked as invalid, wherein the remote station does not accept a connection to a ventilator which wishes to authenticate itself using an authentication file which was created using an invalid combination, so that no transfer of therapeutic data takes place between the ventilator and the remote station and/or the therapeutic data sent from the ventilator to the remote station are not processed by the remote station and/or are discarded by the remote station.

In some embodiments of the method, the remote station generates a message in the event of an authentication attempt of a ventilator using an authentication file made up of an invalid combination of hardware component and ventilator.

In some embodiments of the method, the remote station, in the event of an authentication attempt of a ventilator using an authentication file made up of an invalid combination, transmits a command to the ventilator, which blocks the usage of the ventilator and displays a service message on a display unit of the ventilator.

In some embodiments of the method, a private keycode and a public keycode for the ventilator are generated by the hardware component and the public keycode is transferred as part of the request file to the signing authority, wherein the public keycode is used to encrypt data which are sent to the ventilator and the data encrypted using the public keycode of the ventilator can only be decrypted using the private keycode of the ventilator.

In some embodiments of the method, the remote station has a private keycode and a public keycode, wherein the public keycode is made available to the ventilator as part of an authentication file, wherein the ventilator encrypts data which are transferred from the ventilator to the remote station using the public keycode and wherein the data which were encrypted using the public keycode can only be decrypted using the private keycode.

In some embodiments of the method, the authentication file is created by the signing authority and the signing authority adds a signature code to the authentication file using the private keycode, wherein the ventilator checks the signature code using the public keycode and only accepts the authentication file if the signature code is recognized as originating from the signing authority.

In some embodiments of the method, the hardware component is a mainboard.

The present invention also provides a system comprising at least one ventilator and at least one remote station, wherein the ventilator is configured to establish a connection to the remote station via at least one interface and wherein at least one authentication file is stored on the ventilator, which contains at least one signature code of a signing authority, wherein a public keycode of the signing authority is known to the remote station, wherein the ventilator sends the authentication file to the remote station when establishing a connection to the remote station, wherein the remote station checks the signature code of the authentication file using the public keycode as to whether the signature code originates from the signing point, and wherein therapeutic data are only transferred and/or processed and/or the connection is only established and/or accepted if the remote station recognizes the signature code as originating from the signing authority.

The system is configured and designed to carry out the described method and/or individual method steps.

It is to be noted that the features listed individually in the claims can be combined with one another in any technically reasonable manner and disclose further embodiments of the invention. The description additionally characterizes and specifies the invention in particular in conjunction with the figures.

It is furthermore to be noted that a conjunction "and/or" which is used herein, stands between two features, and links these features to one another is always to be interpreted to mean that in a first embodiment of the subject matter according to the invention, only the first feature can be present, in a second embodiment only the second feature can be present, and in a third embodiment both the first and also the second feature can be present.

Ventilators can be understood as devices in the form of ventilators and diagnostic devices. Diagnostic devices can be used in general to acquire medical parameters of a patient. These also include devices which can acquire and optionally process medical parameters of patients in combination with or exclusively relating to the respiration. A ventilator is to be understood as any device which assists a user or patient in the natural respiration, takes over the respiration of the user or patient and/or is used for respiratory therapy and/or influences the respiration of the user or patient in another manner. These include, for example, but not exclusively, CPAP and bilevel devices (sometimes also known as BiPAP), anesthesia devices, respiratory therapy devices, (clinical, nonclinical, or emergency) ventilators, high flow treatment devices, and coughing machines.

An interface is to be understood in the broadest meaning as any type of device for connection—independent of the type of connection—between the ventilator and a remote station or a person. An interface for a connection between the ventilator and a person can be, for example, a user interface which enables the interaction between person and ventilator directly at the ventilator. Further interfaces can be, for example, interfaces for wireless connection over short (for example, Bluetooth, WPAN, etc.) and/or long distances (mobile wireless, UMTS, 3G, LTE, 5G, WiFi, WLAN, etc.), interfaces for wired connections (inter alia, LAN, USB connections, direct connections to computers, sensors, diagnostic and medical devices), and also plug connections (socket for SD cards, USB terminal, etc.).

The individual components of the ventilator can be divided into modules, wherein the entire ventilator can also be understood as a single module. The definition of a module can be carried out under various aspects which are not explained in more detail at this point and have no influence on the invention as such. An overlap of various modules by the components of the ventilator is also possible here. One component can thus be assigned to two modules, for example. Furthermore, the individual modules can also be combined into module groups, wherein these module groups can also have overlaps under certain circumstances.

The source of a data input can have various forms, but generally results in an electrical signal which can be processed inside the ventilator. For example, the data input can take place mechanically via a user interface in the form of a touch-sensitive display screen. The mechanical touch is converted into an electrical signal, which can be processed in the ventilator, via the touch-sensitive display screen. However, an electrical signal can also be input directly via other interfaces, for example. A precise description of all possible ways of actuating a data input at the ventilator and/or transmitting it via an interface will be omitted at this point, since the form of the data input has no relevance for the method according to the invention or the device according to the invention.

During the handling of the authentication, the ventilator receives a certificate which is used for the authentication of the ventilator and optionally also for the encryption of data using a private key. For this purpose, for example, a corresponding authentication file, thus ultimately a certificate, is created for the ventilator and signed accordingly. The signing, for example by adding a corresponding signature code, is generally carried out by a trustworthy signing authority (certification authority, CA). The authentication is necessary, for example, so that it can be ensured that the data transferred from the ventilator to the remote station also actually originate from the ventilator and it is not pretended that the ventilator sends the data.

During the production of the ventilator, a combination, inter alia, made up of the identification number of the ventilator (for example the serial number of the ventilator), an identification number of a hardware component, and a credential (for example a signature code or a public keycode (public key)) is generated or defined and stored in a database. The identification number of a hardware component can be, for example, the serial number of the mainboard and/or any other individual number/designation of a component, for example serial numbers of a single chip. The validity of this combination can thus be checked again at any later point in time.

If the hardware component, the identification number of which was used to create the authentication, is defective and has to be replaced, initially an invalid combination occurs since it was not yet known during the production of the hardware component (for example mainboard) in which ventilator having which identification number (for example serial number) the hardware component would later be installed. The credential/the keycode (public and private key) for the combination is also not yet created. Therefore, for example, the following steps follow the replacement: Initially the old combination is deregistered from the database by specifying identification number of the ventilator and the hardware components. The replacement of the hardware components is thus enabled at the same time. The identification number of the new hardware components and of the ventilator is then input into the ventilator via an interface (for example, keyboard, touchscreen, etc.). A communication of the combination to a remote station, for example a (credential) server, can then take place via a (different) interface, so that a new credential for the combination is created and/or a corresponding certificate is created/signed. The new combination is also stored in the database.

If the actual private credentials should additionally be made public, for example, due to a data security leak, a new, private credential can thus also be created via this path.

Each ventilator receives a personal certificate (authentication file) during the production, which contains, inter alia, the device serial number (identification number of the ventilator). It is later possible using this certificate that the ventilator can be identified and also authenticated—for example, during online communication or the validation of the therapy data.

The steps required for this purpose are carried out by a test stand PC (checking unit).

The certificate is created as follows:
1. The ventilator has items of information set about the device serial number
2. The ventilator itself generates a key pair and stores the private key so that it can never be read out
3. The ventilator creates a certificate request (CSR, certificate signing request) therefrom
4. The checking unit receives the request and sends this request to the PKI server
5. The PKI server creates the certificate based on the request
6. The PC imports/transfers the certificate to the ventilator Additional items of information about individual components installed in the device are made available to the PKI server.

With the aid of this certificate and the stored key pair, the device can authenticate itself using various modern technologies.

The replacement of a hardware component, the identification number of which was used for generating the authentication file, is described briefly hereinafter on the basis of the example of the mainboard, wherein the process is also transferable to other replaceable components.

After replacement of the mainboard, the device serial number is not to be changed, since among other things the serial number is often used to assign patients to ventilators. The replacement of the mainboard can take place outside the production site, for example at a distributor or service provider, who cannot issue trustworthy certificates or cannot have a trustworthy connection to the PKI of the producer.

Therefore, a method has been developed which opens up the possibility that the customer or distributor can reuse the original serial number after the mainboard has been replaced and can receive a new certificate from the producer without special software or equipment being necessary for the customer/distributor.

Mainboards which are used as replacement mainboards are produced separately as replacement parts and pass through a special final process. During the production of the replacement mainboard, the PKI service already receives items of information about the produced replacement mainboard. The PKI service can be a server which processes everything automatically, but can also comprise persons who carry out individual steps.

During the production, an initialization PC/a checking unit shares the public key (public keycode) and the serial number (identification number) of the replacement mainboard with the PKI service. The following steps are carried out:

Production of the replacement mainboard
1. The checking unit initializes the replacement mainboard and activates the firmware
2. Software is started on this mainboard which generates the key pair (private and public key) and shares items of information about the public key and the serial number of various mainboard components and the mainboard itself with the checking unit. This can take place, for example, via a file (for example in the JSON format) of the checking unit.
3. The checking unit sends these items of information to the PKI service.

Replacement of the mainboard:
1. The defective mainboard is removed, for example by a technician, and a replacement mainboard is installed.

2. The ventilator is started and the (same) serial number of the ventilator is input via an interface.
3. The ventilator generates a request to create/sign a certificate.
4. The serial number (identification number) of the defective mainboard and of the individual components of the mainboard is transferred together with the certificate request (the request file) to the PKI service. For example via email, but it can also take place fully automatically.
5. At the PKI service, it is checked whether the serial number of the components of the old mainboard was combined with the serial number of the ventilator which is to receive a new certificate and whether the public key of the installed replacement mainboard is valid and was acquired during the production at the producer.
6. The certificate is thereupon created based on the new CSR by the PKI service, signed, and stored in a file.
7. The file is transferred to the person who replaces the mainboard and the ventilator can read out and accept the new certificate via an SD card.

According to the invention, it can also be provided that the remote station which is or will be connected to the ventilator also has an authentication file which comprises a signature code generated by the signing point. The ventilator can authenticate the remote station via this signature code.

The authentication according to the invention can also be used, for example, to sign and/or encrypt configuration data for the ventilator. In this case, configuration data are transferred from the remote station to the ventilator. The configuration data are signed, for example, upon creation by the remote station. The ventilator can check the validity and/or integrity and/or the authorization of the configuration data via the signature (for example the signature code). The transfer can take place, for example, via one of the interfaces online (data connection via modem, network, Wi-Fi, Bluetooth, USB, etc.) or also off-line (storage medium, file, USB, etc.). In some embodiments, it can be provided that the configuration data are created by a different remote station than the one via which the configuration data are transferred to the ventilator. For example, the configuration data can be created at a PC which signs the configuration data using the signature code of the PC, wherein the signature code of the PC can be checked by the ventilator to check the authenticity of the configuration data. The configuration data are then transferred, for example, via a server to the ventilator, wherein the server additionally has to authenticate itself at the ventilator and the ventilator also authenticates itself at the server. For example, it can thus be ensured that the configuration data are transferred to the correct ventilator. In some embodiments, it is thus also ensured that the configuration data are only transferred to the intended ventilator.

Alternatively or additionally, it can also be provided that the configuration data are encrypted with the aid of the public key of the ventilator. For example, it can thus be ensured that the configuration data can only be accepted or used by a single ventilator.

The method according to the invention can also be transferred to software modules, for example a firmware update. The software modules are signed accordingly for this purpose, so that the ventilator can authenticate the origin of the software module. In some embodiments, it is optionally provided according to the invention that the ventilator has to authenticate itself at the remote station so that the software module and/or configuration data are transferred. For example, it can thus be ensured that the provided software modules and/or configuration data are only transferred to the intended ventilator.

It can also be provided in software modules which are to be transferred to the ventilator that the software modules are encrypted using the public key of the ventilator, so that only the intended ventilator can use the provided software modules.

In some embodiments, it can be provided that the ventilator comprises functions which are optionally blocked. It can be provided for this purpose that these functions are unlocked, for example, via configuration data. As explained above, these configuration data can be signed and/or encrypted accordingly, so that it can be checked by the ventilator whether the unlocking is permitted. For example, the authenticity of the origin of the configuration data is checked. In some embodiments, the configuration data can also contain data for unlocking an expert and/or service mode. An expert and/or service mode permits, for example, the access to expanded setting options, which are not supposed to be available to a user/patient.

In some embodiments, for example, configuration data can be contained on a data carrier which contain the unlocking of the expert and/or service mode. The ventilator can check the authenticity of the unlocking according to the signature and unlock the respective mode. It can also be provided, for example, that the mode is only activated as long as the data carrier is connected to the ventilator. This can also apply similarly to distant remote stations, the expert and/or service mode only remains activated as long as the distant remote station is connected to the ventilator. It can optionally also be provided that such an expert and/or service mode can be activated/deactivated via the distant remote station, in some embodiments also independently of the connection status between remote station and ventilator.

In some embodiments, it can also be provided that unlocking and/or configuration of modes can take place via the certificate or the authentication file itself. For example, a ventilator can provide the technical conditions for an APAP operation, but is initially configured as a CPAP device. The authentication file can for this purpose contain, in addition to one or more identification numbers, also an item of information as to the type of ventilator the device is to be configured as. For example, the ventilator receives an updated certificate having the new items of information for this purpose. Alternatively or additionally, it can also be provided that a corresponding unlocking code is contained in the certificate or the authentication file which is downloaded onto the ventilator.

The method according to the invention also permits, inter alia, a unique identification of the ventilator and a simultaneous authentication. It can thus also be ensured, for example, that in addition to the origin of the data from the ventilator, data which are exclusively intended for the ventilator can also be accurately transferred. If the ventilator authenticates itself, for example, at a remote station or is authenticated by the remote station, it can also be checked again via the unique identification whether data for the ventilator are present and are to be transferred.

Alternatively or additionally, the method according to the invention can also be used to implement an authorization between the user of the ventilator and a remote station on the basis of a "challenge-response" method. For example, the user uses a remote station, such as a smart phone having an app, together with the ventilator and also wishes to connect via the app to another remote station, for example a server and/or a remote support. The certificate of the ventilator can thus also be used for the authentication of the user of the ventilator. It can be ensured at the remote station by the signing and/or encryption of a "challenge" requested by the remote station that the user of the remote station is in possession of a single ventilator—for example having a specific serial number (identification number)—and access to certain functions and/or privileges can be allowed to him. For example, it can thus also be ensured that messages are transferred securely between user and caregiver.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

The method according to the invention for authentication is explained in more detail on the basis of exemplary embodiments in FIGS. 1 to 7. In FIGS. 2 to 7, components of the ventilator and devices/units are not described further for reasons of comprehensibility. The presence of the components which are to be assigned at least as standard features to a ventilator or the corresponding remote stations and can be necessary for executing the method, for example corresponding interfaces, is implied here.

Figure 1:
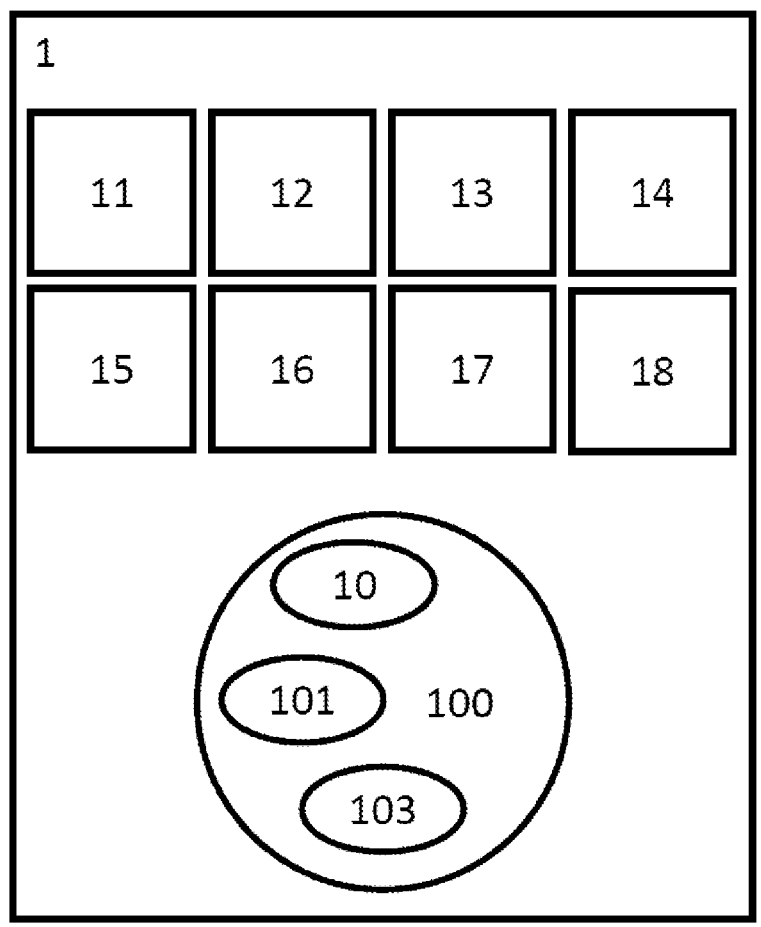
FIG. 1 shows a ventilator by way of example.
Figure 1:
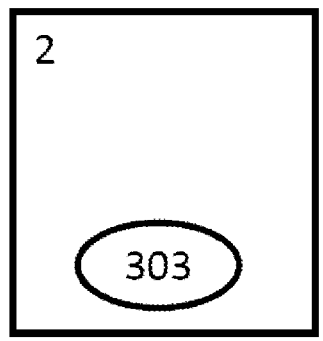

FIG. 1 shows by way of example a ventilator 1 having an interface 11, the hardware components 12, for example a mainboard, a display unit 13, a sensor unit 14, a control unit 15, a fan/valve unit 16, a processing unit 17, and a storage unit 18. Moreover, an authentication file 100, which contains a signature code 10, for example a hash value, is stored on the ventilator. Furthermore, a remote station 2 is shown, to which at least the public keycode 303 of a signing authority 3 (not shown in FIG. 1) is known. The remote station 2 can be a server, an app, a program, a computer, a smart phone, and/or further devices which are designed to establish a connection to the ventilator 1.

The sensor unit 14 is configured to acquire measured values, in particular parameters, which are related to a respiratory flow, a respiratory volume, a respiratory frequency, an inhalation and exhalation duration, a respiratory contour, a leak, or a treatment pressure. The sensor unit 14 can optionally perform additional measurements of components or the temperature of the respiratory gas or the blood. The sensor unit 14 transfers the acquired measured values to the processing unit 17.

The processing unit 17 can process the acquired measured values. For example, the processing unit 17 can carry out smoothing, artifact filtering, or downsampling of the measured values. For example, the processing unit 17 is embodied as a combined processing, calculation, and recognition unit. The above-mentioned units can also be embodied, for example, as individual units, however. The calculation unit calculates signals and/or characteristic variables from the measured values acquired by the sensor unit 14 and processed by the processing unit 17, for example a mean value, a median, a percentile, a derivative, a frequency distribution, a duration or a fraction of exceeding or falling below threshold values. The recognition unit is configured to recognize events/states, for example alarms, breathing interruptions, artifacts, coughing, oxygen (de-)saturations, asynchronism between device and user, inhalation, exhalation, or mandatory breaths.

The storage unit 18 stores, inter alia, the values/parameters acquired by the sensor unit 14 and/or the values, data, and/or items of information processed by the processing unit 17 and/or the calculation unit, or stores them at least temporarily. The items of information, data, and values obtained by the recognition unit can and/or are also at least temporarily stored in the storage unit. Temporary storage means, for example, that the values, data, and/or items of information are stored until a transfer and are then, for example, deleted or unlocked to be overwritten.

The control unit 15 is used, for example, to control the ventilator 1, in particular a fan and/or valve unit 16 for generating the respiratory gas flow or ventilation pressure. The control unit 15 can also be designed to control other components and/or units of the ventilator 1. In some embodiments, the control unit 15 can also be further divided and can consist of multiple control units, which each control an individual unit and/or component of the ventilator 1.

The interface 11 is configured, for example, to establish a network connection to the remote station 2. The interface 11 can be designed as a wired or wireless interface for this purpose. The ventilator 1 can moreover have a plurality of interfaces in some embodiments. Inter alia, the interfaces can be selected from the following groups:

a. wireless interface for long distances (mobile wireless, LPWAN, WLAN) for example for telemonitoring, tele-service, tele-setting, FW update b. wireless interface for short distances (Bluetooth, WPAN) for example for remote control via app, feedback on the treatment in the app, service processes; connection to diagnostic devices (polygraphy), FW update/firmware updating c. user interface (User Interface, GUI, Touch Screen) for example for operation, feedback, service d. wired interfaces, for example for remote control in sleep laboratory, reading out more detailed treatment data, connection to diagnostic devices (PSG), external terminal of a radio module, service, communication with the test stand, FW update e. storage medium/terminal for USB stick, SD card, etc.

The hardware component 12 embodied by way of example as a mainboard (main circuit board) is used, inter alia, as a central electronics component to which further electronics components are connected. For example, at least the storage unit 18, the interface 11, the control unit 15, and the components that are not shown such as processor, working memory (RAM), BIOS chip, etc. are connected to the mainboard 12 and/or partially installed on the mainboard.

The display unit 13 can display and play back, for example, values, data, and items of information of the ventilator 1. In some embodiments, the display unit 13 can be embodied as a touch-sensitive display screen (touch-screen), via which in addition to the display and playback, the input of data and items of information into the ventilator 1 is also possible.

An authentication file 100 is stored on the ventilator 1, which contains, for example, a signature code 10, the identification number 101 of the ventilator 1, and a public keycode 103. The identification number 101 can be, for example, the serial number of the ventilator 1, which is assigned during the production of the ventilator. The public keycode 103 is created, for example, by the mainboard 12 of the ventilator 1 together with the private keycode 103', for example during the activation/initiation of the mainboard 12 during or after the production of the ventilator 1. The keycodes 103, 103' are generated here, for example, via routine generating methods, which are known in the field of asymmetrical cryptography. The signature code 10 was generated by a signing authority 3 (not shown in FIG. 1) by using the private keycode 303' of the signing authority 3 and added during the production of the ventilator 1 to the authentication file 100. The signing authority 3 represents a trustworthy authority here, via which it can thus be confirmed that the authentication file 100 is real and also the content of the authentication file 100 is thus trustworthy. The authentication file 100 thus represents a certificate, inter alia, about the identity of the ventilator 1 which is checked and signed by a third trustworthy authority. Trustworthy signing authorities (also called "certification authority", abbreviated CA) can be governmental, official, or also commercial institutions, for example also the producer of the ventilator 1, which operates a signing authority 3, for example, to sign correspondingly corresponding authentication files 100 of the ventilators 1 produced by it.

The signature code 10 can be checked, for example, via a public keycode 303 of the signing authority 3. A remote station 2, if the public keycode 303 is known to the remote station 2, can thus, for example, check whether the authentication file 100 from the ventilator 1 is trustworthy, thus that the authentication file 100 was checked and finally was provided with the signature code 10 by the trustworthy signing authority 3.

During the establishment of the connection between the ventilator 1 and the remote station 2, the authentication file 100 is checked by the remote station 2 according to a standard protocol for establishing connections, for example an SSL protocol or TLS protocol. If the remote station 2 recognizes the signature code 10 as originating from the signing authority 3, the authentication file 100 is thus accepted as trustworthy, the ventilator 1 is thus authenticated, and the connection to the ventilator 1 is accepted and established.

The signing authority 3 can be, for example, a single computer or server, in some embodiments the signing authority 3 is also to be understood as a system made up of multiple computers and/or servers. In particular, the signing authority 3 can also be, for example, a PKI service (for example at least consisting of certification authority and request authority).

The remote station 2 comprises, for example, a user database or is connected to a user database. If the ventilator 1 connects to the remote station 2, the remote station 2 can assign the ventilator 1 to a user, for example, on the basis of an identification number 101 of the ventilator 1 which is contained in the authentication file 100. Due to the prior authentication of the ventilator 1 at the remote station 2, it can thus be ensured, for example, that the transferred data actually originate from the ventilator In some embodiments, the remote station 2, for example embodied as a simple smart phone app for reading out the data of the ventilator 1, does not comprise a user database. An authentication for establishing the connection is nonetheless necessary here.

Figure 2:
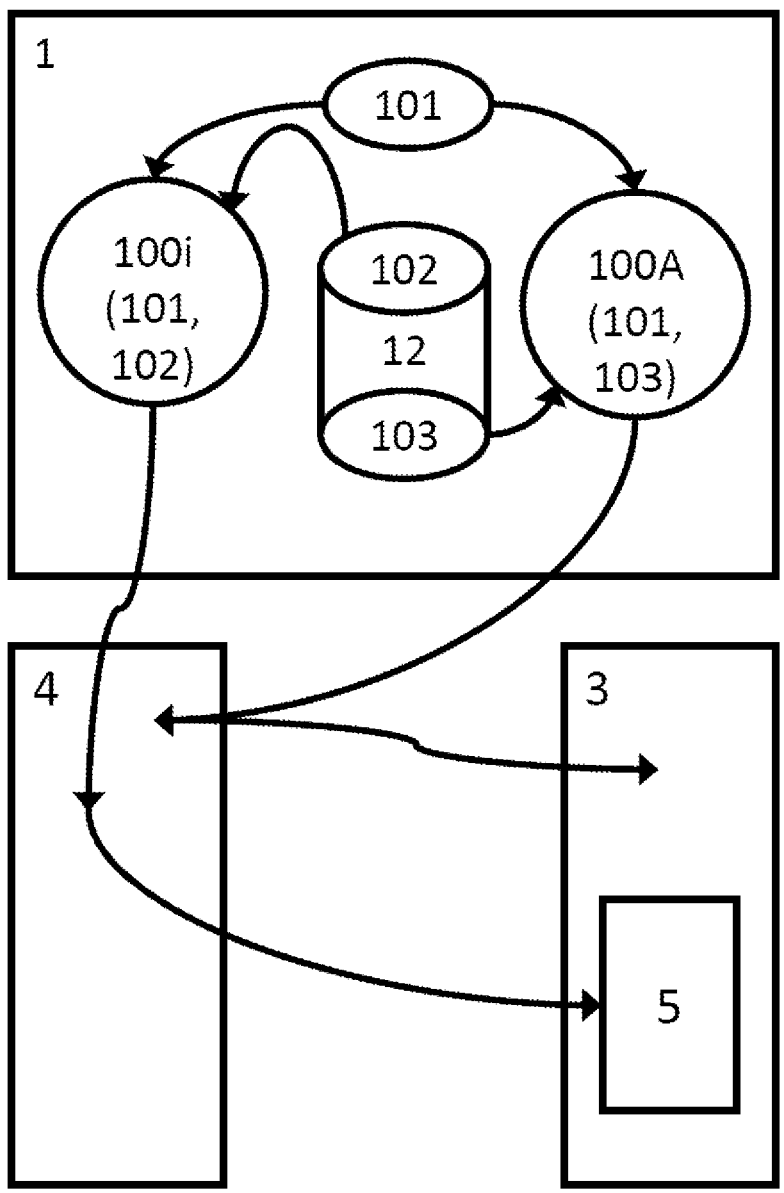
FIGS. 2 and 3 illustrate by way of example how an authentication file is generated during the production of the ventilator.
Figure 3:
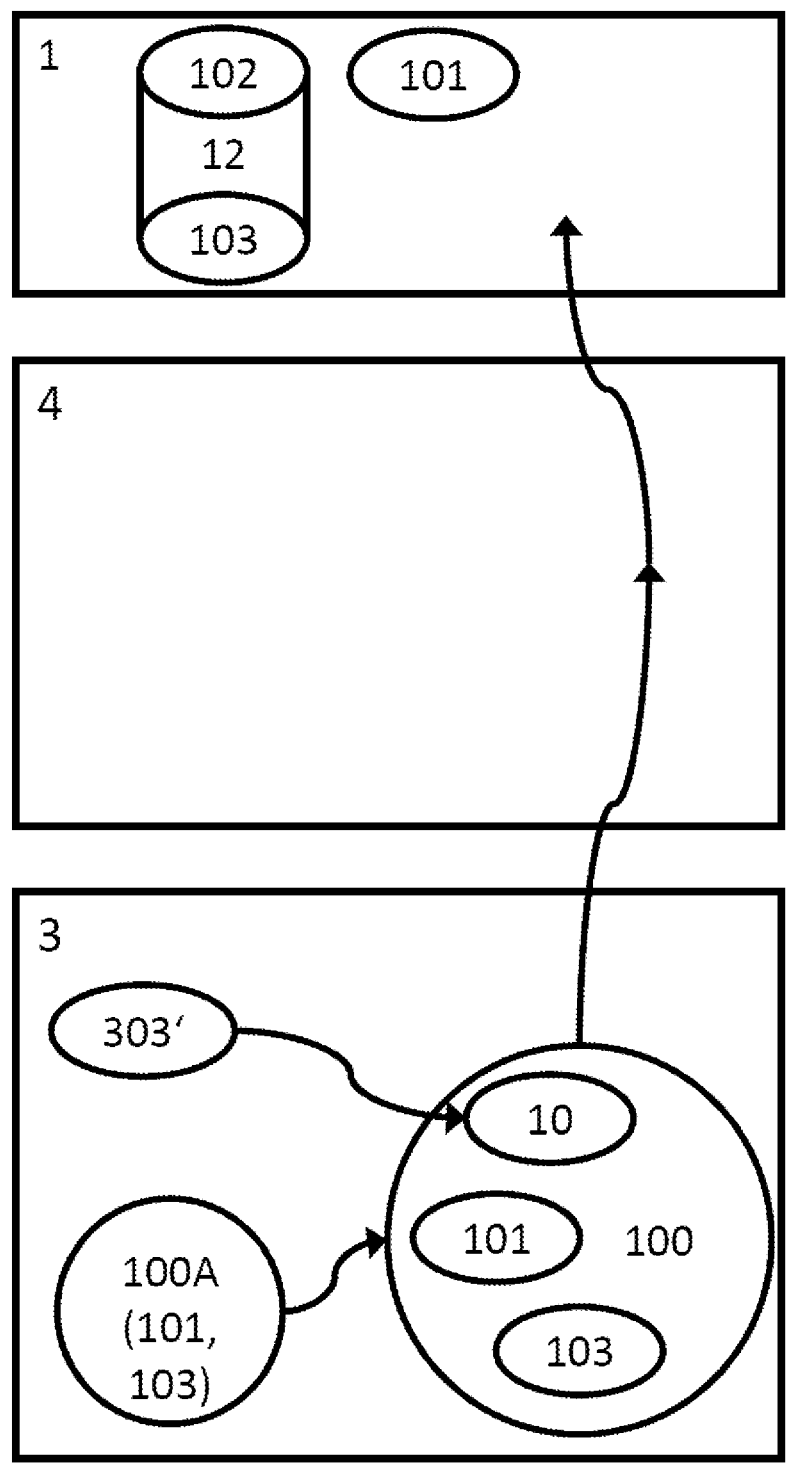
Figure 4A:
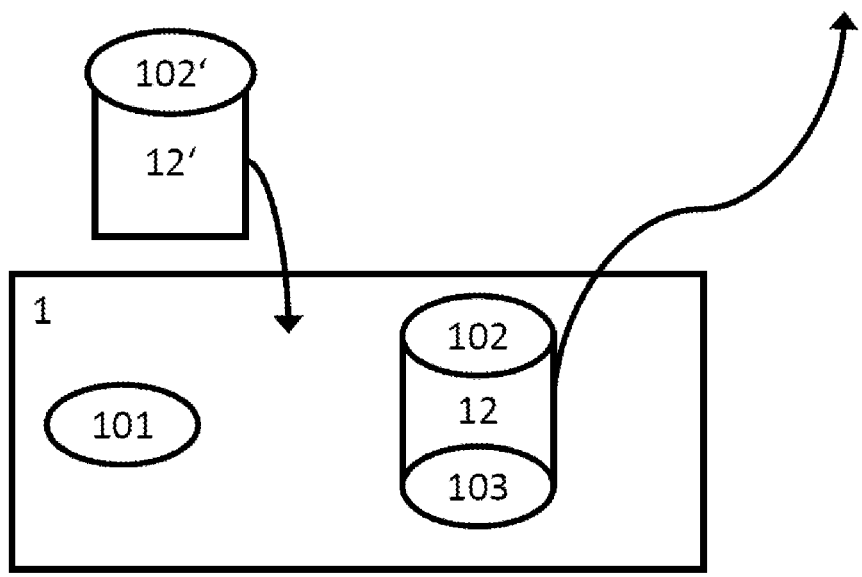
FIGS. 4A, 4B, 5, and 6 illustrate by way of example the steps of replacing a hardware component (of a mainboard) with another hardware component.
Figure 4B:
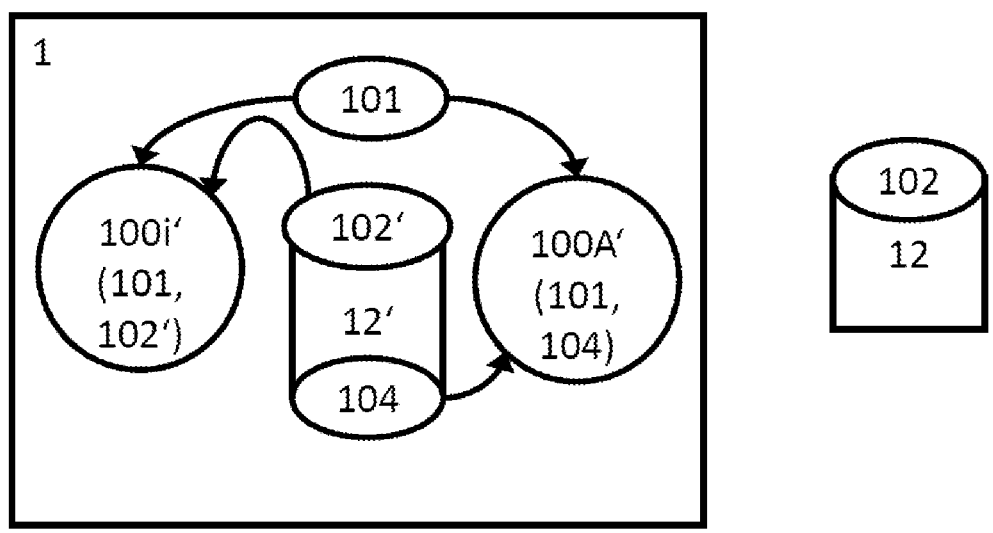

It is shown by way of example in FIGS. 2 and 3 how the authentication file 100 is generated during the production of the ventilator 1. During the first initialization/activation of the ventilator 1 or the mainboard 12, a pair of keycodes 103, 103' is created, which are associated directly with the mainboard 12 or are stored directly on the mainboard 12. During the first activation, moreover the identification number 101 of the ventilator 1 is input via a user interface (for example a display unit 13 embodied as a touch screen, a memory card, a smart phone app, etc.) and made available to the ventilator 1. The ventilator 1 thereupon creates two files 100A and 100i: a request file 100A, using which the authentication file 100 is generated, and the information file 100i, which contains items of information about the ventilator 1. Both files 100A, 100i are transferred to a checking unit 4, which is connected to the ventilator 1, for example, primarily for checking for functionality. The information file 100i contains at least the identification number 101 of the ventilator 1 and the identification number 102 of the mainboard 12 here. The request file 100A contains at least the generated public keycode 103 and the identification number 101 of the ventilator 1. Moreover, a list 5 is stored on the signing authority 3, which comprises valid and/or known combinations of ventilators 1 and mainboards 12 and/or the identification numbers 1, 12 thereof. In some exemplary embodiments, the list 5 is not stored on the signing authority 3, but rather saved in a database or on a data server to which the signing authority 3 has access. It is checked on the basis of the list 5 whether the combination of the ventilator 1 with the mainboard 12 is a combination that is already present and is valid and/or enabled. If the combination is not yet present but is valid/enabled, the combination 101 is thus entered with 102 or 1 with 12 in the list 5, as schematically indicated in FIG. 3. If the combination is a valid combination, the authentication file 100 is created using the request file 100A via the signing point 3.

It is furthermore schematically indicated in FIG. 3 that the signing authority 3 creates the authentication file 100 from the request file 100A and adds it to the signature code 10 using the private keycode 303'. The creation of the signature code 10 thus takes place so that the signature code 10 can at least be checked for the origin by the signing authority 3 using the public keycode 303 of the signing authority. In some embodiments, the signature code 10 is additionally tailored to the authentication file 100, thus only matches with this authentication file. After creation of the authentication file 100, it is transferred to the checking unit 4 and from there to the ventilator 1.

In some exemplary embodiments, the method steps are configured so that—if possible—the method runs fully automatically. Thus, for example, only the input of the identification number 101 at the ventilator 1 would need to be carried out manually, since it is not yet electronically present in the ventilator 1 at the time of the first activation. In some embodiments, for example, it can also be provided so that individual steps have to be at least initiated and/or carried out manually. The transfer of the request file 100A to the signing authority 3 is to be mentioned as an example, which in some embodiments first requires a manual confirmation at the checking unit 4. Moreover, it is also conceivable, for example, that the checking of the list 5 for present, valid, and enabled combinations of ventilator 1 and mainboard 12 is carried out manually. In some exemplary embodiments, multiple or all steps are initiated and/or carried out manually.

The creation of the signing code 10 by the signing authority 3 using the private keycode 303' takes place, for example, in consideration of known and/or routine methods from the field of Private/Public Key Infrastructure (PKI).

If the hardware component/the mainboard 12 is replaced with a new hardware component/a new mainboard 12', the authentication file 100 including the pair of keycodes 103, 103' thus also has to be updated, which are stored, for example, directly on the mainboard 12. The steps of the replacement are shown by way of example in FIGS. 4A, 4B, 5, 6. It can be seen in FIG. 4A by way of example that with the replacement of the mainboard 12, the identification number 102 of the mainboard 12 and the keycodes 103, 103' (latter not shown) are also removed. In some embodiments, the authentication file 100 is moreover also stored on the mainboard 12, which is also lost with replacement. In addition, the authentication file 100 also becomes invalid, since it is created based on a combination of at least the public key 103 and the identification number 101. Upon the first activation of the new mainboard 12', for example during the production as a replacement component or after installation in the ventilator 1, a public keycode 104 and a private keycode 104' are again generated by the mainboard 12'. In some embodiments, the mainboard 12' is already activated and/or initiated at the producer, wherein the keycodes 104, 104' are created. For example, in some embodiments the identification number 101 of the ventilator 1 has to be input during or after the activation of the mainboard 12'. During and/or after the activation of the mainboard 12, the information file 100*i*', which contains at least the identification numbers 101, 102', and the request file 100A', comprising at least the public keycode 104 and the identification number 101, are also created.

Figure 5:
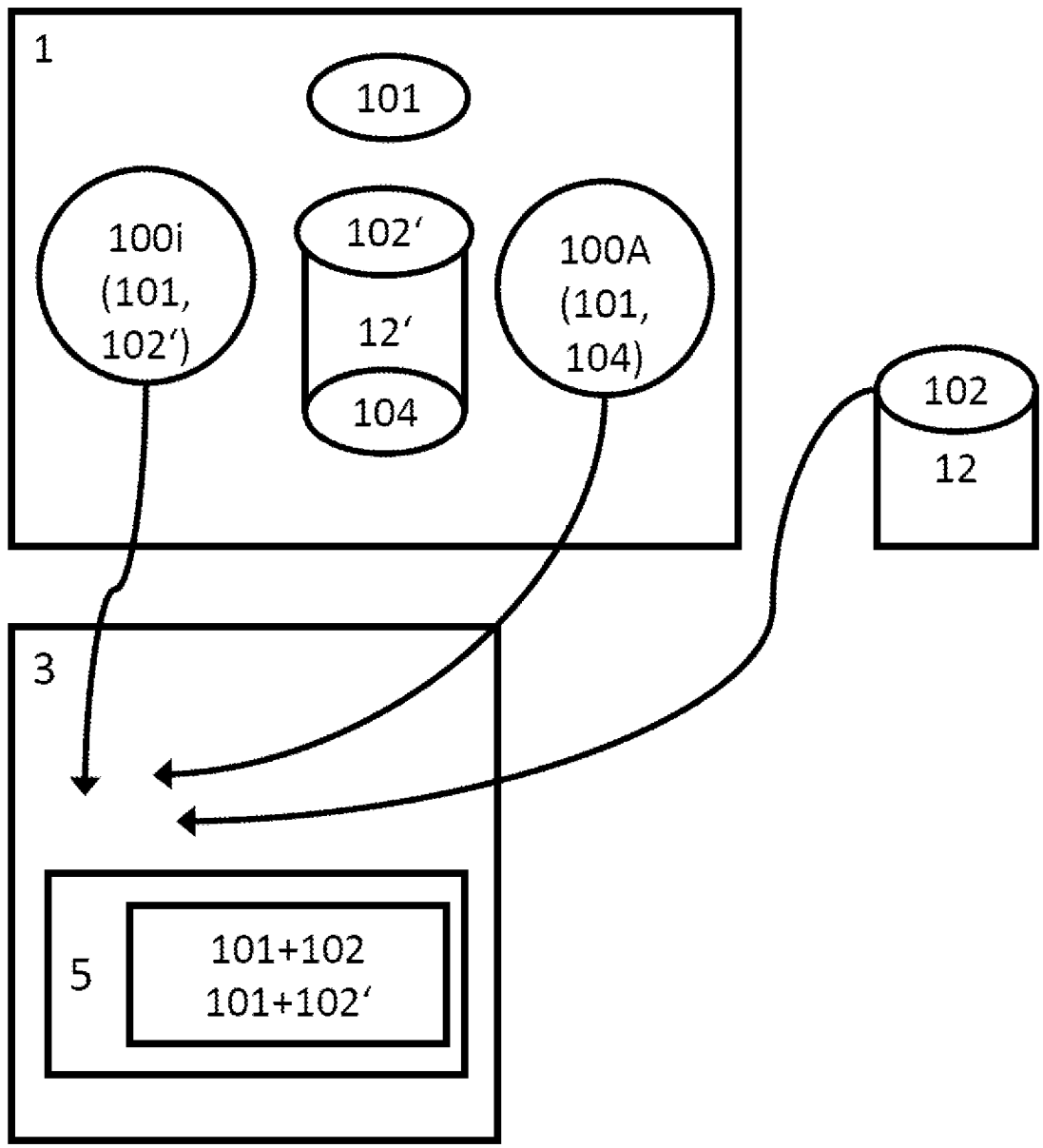
Figure 6:
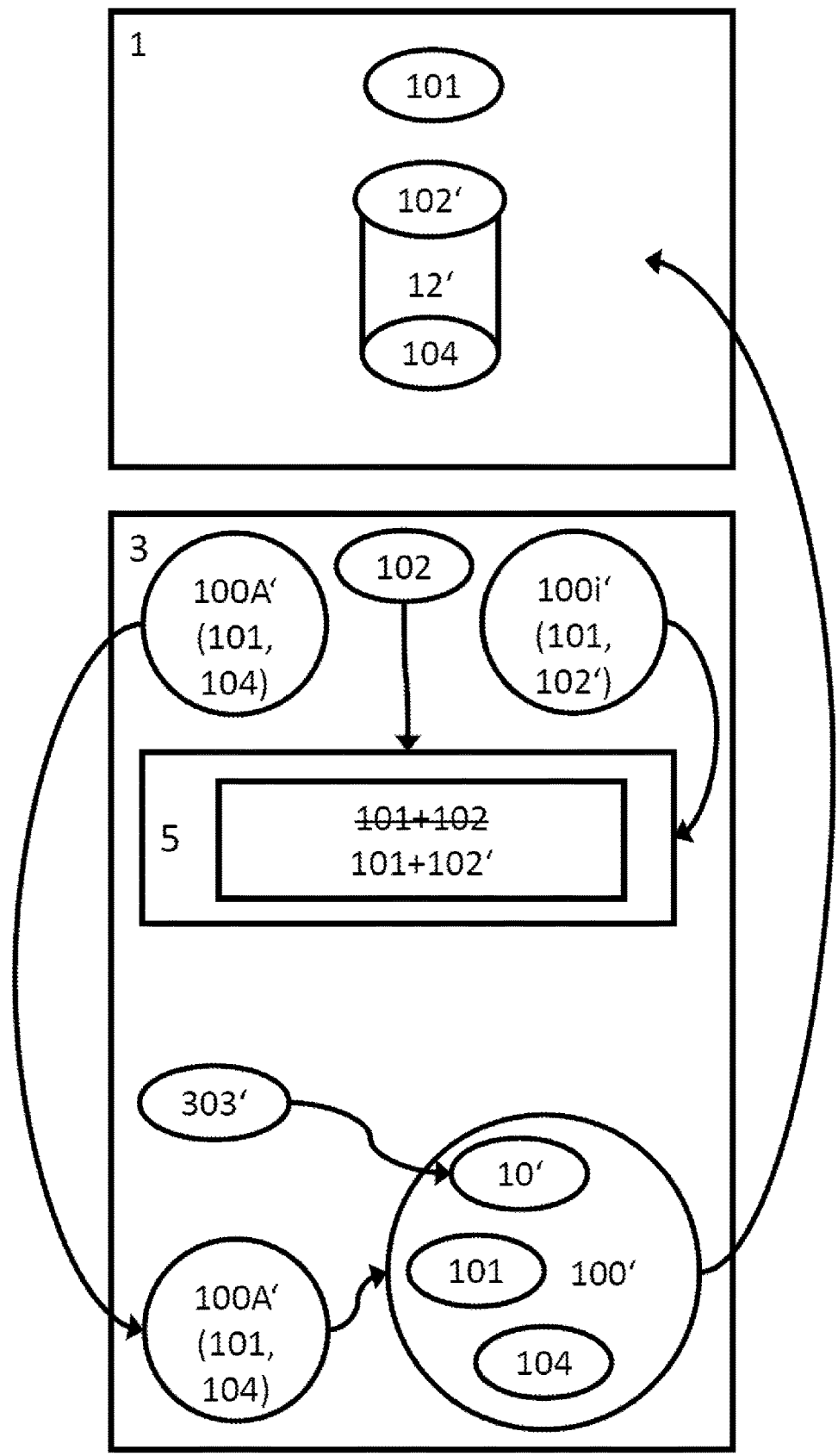

In a further step, illustrated by way of example in FIG. 5, the files 100*i*', 100A' and the identification number 102 of the old mainboard 12 are transferred to the signing authority 3. The signing authority 3 thereupon checks whether the old combination of the ventilator 1 with the mainboard 12 was a valid combination, for example on the basis of the identification numbers 101, 102. The identification number 102 is, for example, not only stored electronically on the mainboard 12, but also printed/stickered on the component. The valid combinations are stored, for example, in the list 5, which is stored, for example, directly on the signing authority 3, but can also be saved or stored, for example, in a database or a server. It is also saved, for example upon request for a new mainboard 12' by a service technician or a distributor, that the mainboard 12' is enabled for a combination with a ventilator. For example, for this purpose the new combination of 101 and 102' is entered as an enabled combination in the list 5. For some embodiments, it is also conceivable that the mainboard 12' is enabled in general for the combination with a ventilator. For example, if multiple new mainboards are requested by a distributor or service technician, these can be combined "freely" with the ventilators, without the technician having to ensure exactly which ventilator is combined with which mainboard. For example, during the request (ordering) of the new mainboards, the identification numbers of the ventilators, which are to receive a new mainboard, can also already be requested. The new mainboards can thus be enabled for only precisely these ventilators. A combination with other ventilators would be recognized as nonvalid upon checking of the list 5 and accordingly no authentication file would be created for just this combination. The check as to whether the new mainboard 12' can be combined with the ventilator 1 or an authentication file 100' is created can take place, for example, automatically by the signing authority 3 using the identification numbers 101, 102, 102'. In some embodiments of the method, a manual check of the combinations can also take place.

In some embodiments of the method, the items of information about valid combinations of ventilators and mainboards and general data such as the public keycode and the identification number of the mainboard are saved on the signing authority 3 or at least accessible to the signing authority 3.

For example, during the production of the new mainboard 12', which is provided as a replacement part, this mainboard is already initialized. This means that the mainboard 12' already generates at least the public keycode 104 at this point in time and moreover transfers items of information about at least the identification number 102' and the keycode 104 to the signing authority 3 or these items of information are transferred. The signing authority 3 can thus check at a later point in time whether the new mainboard 12' is provided for use in a ventilator.

If the combination of the ventilator 1 with the mainboard 12' is recognized as enabled or valid, the request file 100A' is thus transferred to the signing authority 3. The signing authority 3 thereupon creates the authentication file 100' from the request file 100A' and adds the signature code 10' to this authentication file 100' using the private keycode 303'. The authentication file 100' can then be transferred directly to the ventilator 1, for example, according to FIG. 6.

Furthermore, the old combination of ventilator 1 and mainboard 12 or the corresponding identification numbers 101, 102 is deleted from the list 5 and/or marked as out of date and invalid, for example. In some embodiments, there can moreover also be a further list and/or database in which out of date and/or invalid authentication files are noted. In addition, it is conceivable that additionally a further list/database is managed in which known, invalid combinations are noted. In particular, a list having out of date and/or invalid authentication files can be provided, for example, to the remote station 2, so that the remote station 2 can additionally check whether the authentication file 100, 100' sent by the ventilator 1 is presently valid.

In some embodiments, to create a new authentication file 100', no information file 100*i*' is created and/or transferred to the signing authority 3, but rather the required data are communicated to an employee of the producer or operator of the signing authority 3, who manually performs the changes on list 5 and/or additional lists/databases. It is also possible to transfer directly from the ventilator 1 to the signing authority 3, for example via a data carrier, or via other pathways.

If a ventilator 1 connects to the remote station 2 and sends, for example, an authentication file 100, based on the combination of the ventilator 1 with the mainboard 12, although the combination of 1 and 12 is not a presently valid combination, the remote station 2 thus cannot accept the connection to the ventilator 1, therefore no connection takes place. In some embodiments, the remote station 2 sends a corresponding message at least to the ventilator 1 in the case of an invalid authentication of the ventilator 1. This message can contain various items of information, for example a notification that the authentication file 100 is invalid and/or a notification that a service hotline is to be contacted. For example, a command can also be sent to the ventilator 1 upon use of an invalid authentication file 100, which results in blocking of the ventilator 1, which is accompanied by a corresponding message on the display unit 13 of the ventilator 1.

Figure 7:
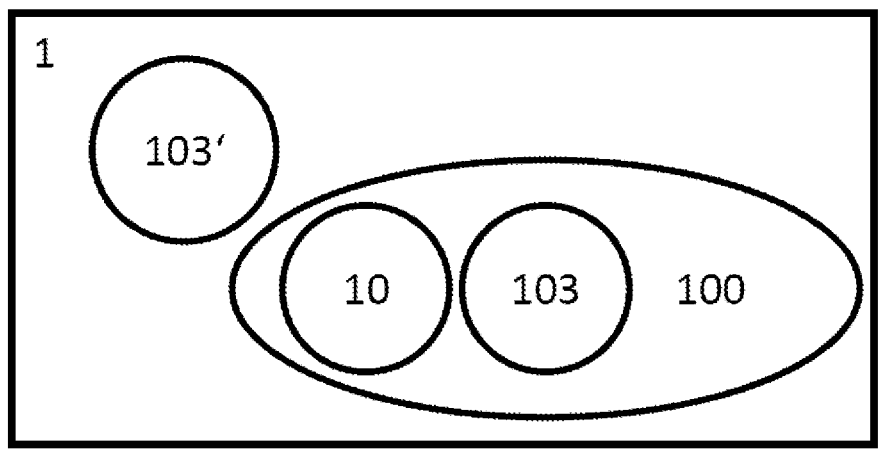
FIG. 7 schematically illustrates how an authentication file, which also contains a signature code generated by a signing point, is stored on a remote station of the ventilator.
Figure 7:
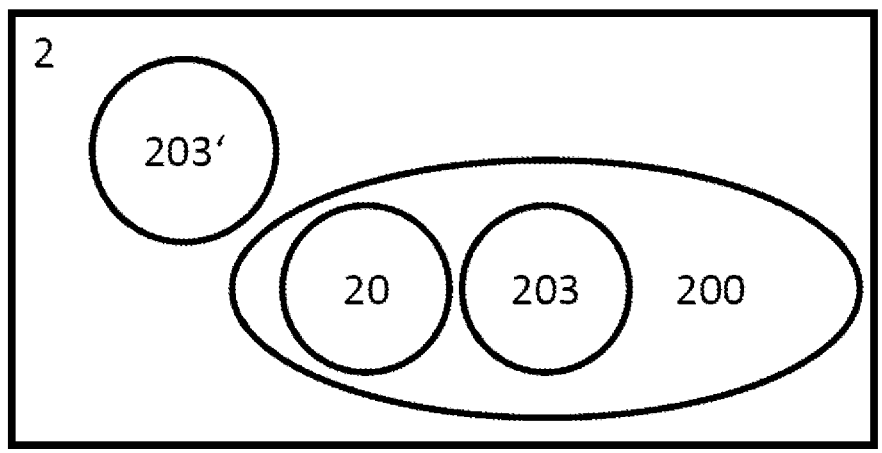

In some embodiments, an authentication file 200 is also stored on the remote station 2, which also contains a signature code 20 generated by the signing point 3, as schematically shown in FIG. 7. The ventilator 1, and also other remote stations, can check, if the public keycode 303 of the signing authority 3 (not shown) is known, whether the signature code 20 was actually created by the signing point 3 and can thus authenticate the remote station 2. Moreover, the authentication file 200 contains a public keycode 203. The authentication file 200 can be transferred, inter alia, in the case of a connection to the ventilator 1. If data are to be transferred from the ventilator 1 to the remote station 2, these data can thus be encrypted, for example, using the public keycode 203 of the remote station 2. Data which were encrypted using the public keycode 203 can be decrypted again only using the private keycode 203', for example. Vice versa, the remote station 2 can also use the public keycode 103 of the ventilator 1 to encrypt data, which can only be decrypted again by the private keycode 103'.

This can relate by way of example but not exclusively to configuration data for the ventilator 1. It can be provided, for example, that the remote station 2 signs the configuration data using the signature code 20. The ventilator 1 can authenticate the configuration data, for example via the public keycode 303 of the signing authority 3.

Upon successful authentication, the configuration data can then be accepted or used. If the transfer of the configuration data takes place, for example, from a distant remote station 2 to the ventilator 1, it can be provided that the ventilator 1 first has to authenticate itself at the remote station 2. It can thus also be ensured that the configuration data are only transferred to the ventilator 1 provided for them.

Furthermore, it can be provided that the configuration data are encrypted using the public key 103 of the ventilator 1, so that these data can exclusively be decrypted using the private key 103' of the ventilator 1. The transferred configuration data can accordingly only be used by the ventilator 1.

LIST OF REFERENCE SIGNS

1 ventilator
2 remote station
3 signing authority
4 checking unit
5 list
10 signature code
10' signature code
11 interface
12 hardware component/mainboard
12' hardware component/mainboard
13 display unit
14 sensor unit
15 control unit
16 fan/valve unit
17 processing unit
18 storage unit
20 signature code
100 authentication file
100' authentication file
100A request file
100A' request file
100i information file
100i' information file
101 identification number
102 identification number
102' identification number
103 public keycode
103' private keycode
104 public keycode
104' private keycode
200 authentication file
203 public keycode
203' private keycode
303 public keycode
303' private keycode

What is claimed is:

1. A method for authenticating at least one ventilator with at least one remote station, the ventilator being capable of connecting itself via at least one interface to the at least one remote station, wherein the method comprises:
   storing at least one authentication file on the ventilator, which authentication file contains at least one signature code of a signing authority, a public keycode of the signing authority being known to the at least one remote station,
   sending the authentication file to the at least one remote station by the ventilator when establishing a connection to the at least one remote station, the remote station checking the signature code of the authentication file using the public keycode as to whether the signature code originates from the signing authority, and
   authenticating the ventilator when the at least one remote station recognizes the signature code as originating from the signing authority;
   transferring therapeutic data from the ventilator to the at least one remote station, and
   discarding the transferred therapeutic data by the at least one remote station if the remote station does not recognize the signature code as originating from the signing authority.

2. The method of claim 1, wherein therapeutic data are transferred from the ventilator to the at least one remote station after and/or during establishment of the connection, the therapeutic data being only processed by the at least one remote station when the ventilator is authenticated.

3. The method of claim 1, wherein the method further comprises creating by the signing authority the authentication file and adding the signature code to the authentication file using a private key of the signing authority.

4. A system comprising at least one ventilator and at least one remote station, wherein the ventilator is configured to establish a connection to the at least one remote station via at least one interface, the system comprising:
   a ventilator having an interface and a hardware component, wherein the hardware component is a mainboard; and having stored thereon:
   a public keycode of a signing authority and at least one authentication file wherein the public keycode of the signing authority is known to the at least one remote station,
   the ventilator further being configured to send the authentication file to the at least one remote station when establishing a connection to the at least one remote station, the remote station being configured to check the signature code of the authentication file using the public keycode as to whether the signature code originates from the signing authority, and the remote station being further configured to authenticate the ventilator when the at least one remote station recognizes the signature code as originating from the signing authority, the ventilator being further configured to transfer therapeutic data to the at least one remote station; and the remote station being further configured to discard the transferred therapeutic data if the remote station does not recognize the signature code as originating from the signing authority.

\* \* \* \* \*